United States Patent
Magidson

(10) Patent No.: US 7,107,993 B2
(45) Date of Patent: Sep. 19, 2006

(54) EARPLUG

(75) Inventor: Mark Magidson, Los Angeles, CA (US)

(73) Assignee: Moldex-Metric, Inc., Culver City, CA (US)

( * ) Notice: Subject to any disclaimer, the term of this patent is extended or adjusted under 35 U.S.C. 154(b) by 353 days.

(21) Appl. No.: 10/987,225

(22) Filed: Nov. 12, 2004

(65) Prior Publication Data
US 2006/0102418 A1    May 18, 2006

(51) Int. Cl.
*A61F 11/00* (2006.01)

(52) U.S. Cl. .................. 128/864; 128/857; 181/129; 181/130; D24/106

(58) Field of Classification Search ............... 128/857, 128/864, 865; 181/129, 130; D24/106
See application file for complete search history.

(56) References Cited

U.S. PATENT DOCUMENTS

| | | | | |
|---|---|---|---|---|
| D298,356 S | * | 11/1988 | Falco | D24/106 |
| D340,282 S | * | 10/1993 | Leight | D24/106 |
| D341,656 S | * | 11/1993 | Leight | D24/106 |
| D405,521 S | * | 2/1999 | Leight | D24/106 |
| D423,664 S | * | 4/2000 | Falco | D24/106 |
| D427,304 S | * | 6/2000 | Magidson et al. | D24/106 |
| 6,345,684 B1 | * | 2/2002 | Leight | 181/135 |
| D466,995 S | * | 12/2002 | Knauer et al. | D24/106 |
| D493,219 S | * | 7/2004 | Falco | D24/106 |
| D496,722 S | * | 9/2004 | Falco et al. | D24/106 |

* cited by examiner

Primary Examiner—Fadi H. Dahbour
(74) Attorney, Agent, or Firm—Charles H Schwartz

(57) ABSTRACT

An earplug composed of an injected molded resilient polymeric material for insertion into an ear canal by a fingertip of a user, including an elongated member having a nose portion formed as a curved front end. An open cup shaped rearward extending flange located at the end of the elongated member opposite to the nose portion and with the open cup shaped rearward extending flange configured to receive the fingertip of the user. The elongated member including at least one flange element located intermediate the nose portion and the open cup shape flange. The nose portion and the flange element having a generally curved shape to extend into and conform to the wall of the ear canal. The earplug composed of a resilient polymer material having a relatively low Shore A Durometer hardness value and the cup shape flange portion with the inserted fingertip of the user forming a handle of greater stiffness to enable the earplug with the relatively low Shore A Durometer hardness value to be more easily inserted into the ear canal.

24 Claims, 2 Drawing Sheets

EARPLUG

BACKGROUND OF THE INVENTION

1. Field of the Invention

The present invention relates to an earplug and more specifically is directed to an injection molded resilient thermoplastic elastomer (TPE) earplug having at least one flange and useful as a hearing protector.

2. Description of the Prior Art

There are presently on the market a number of earplugs that include a central shaft and extending there from at a nose end at least a single flange. The earplugs are generally composed of an injection molded resilient thermoplastic elastomer material such as synthetic rubber material. The flange element extends outwardly from the nose end of the shaft member and also extends rearward from the nose end and is so spaced so as to provide a free annular space between the flange and the shaft. One basic earplug of this type is generally referred to as the V-51R earplug and was developed during the course of World War II in order to provide improved hearing protection to members of the military who were subjected to excessive sound.

In use, the earplug is forcibly inserted into the ear canal, thereby at least partially collapsing the rearward extending flange element into the underlying free annular space and conforming the flange element into an acoustic sealing relationship to the walls of the ear canal.

Three of the important criteria for any earplug of this type, in addition to sound attenuation, are ease of insertion into the ear canal, comfort during use and ease of removal when appropriate. In general, softer polymers are more comfortable in use for obvious reasons and harder materials, while less comfortable, are easier to insert into the ear canal.

An improved triple flange version of this type of earplug is shown in U.S. Pat. No. 4,867,149 listing Robert N. Falco as the inventor and issued on Sep. 19, 1989. This patent gives further background information on the V-51R earplug and other prior art earplugs of this type. In addition U.S. Pat. No. Des 253,723 issued on Dec. 18, 1979 listing Howard S Leight as the inventor, also shows a triple flange earplug, which is currently on the market.

The prior art earplugs of the type disclosed above typically have a number of problems. For example, the earplug shown in U.S. Pat. No. 4,867,149 has a solid shaft member to support the multiple flanges and this type of earplug can create discomfort in a significant proportion of the wearer population. This discomfort would generally be perceived as a sense of excessive pressure being brought to bear on the walls of the ear canal because of the central solid shaft member not flexing adequately to the curvature of the car canal. The central solid shaft member, however, does have the advantage of allowing the earplug to be fully inserted into the ear canal as long as the material used to make the earplug of the U.S. Pat. No. 4,867,149 is of a sufficient hardness to allow for this full insertion.

The product on the market made in accordance with U.S. Pat. No. Des. 253,723 are generally of a softer material than the product made in accordance with the U.S. Pat. No. 4,867,149. In addition the product made in accordance with the U.S. Pat. No. Des. 253,723 is hollow at the tip and therefore is more comfortable in the ear. However, since the product made in accordance with the U.S. Pat. No. Des. 253,723 is of a softer material, it is difficult to insert this earplug fully into the ear since the rear end of the earplug does not have sufficient stiffness for the user to fully insert the earplug into the ear.

It would therefore be desirable to have an earplug, which is comfortable in the ear, includes at least a single flange member and yet has sufficient rigidity at a rear end portion to enable the user to fully insert the earplug into the ear. U.S. Pat. No. 5,957,136 overcomes the problems of the above prior art earplugs by using a two-piece construction. This construction includes front and rear members. One member, located at the rear, forms part of the shaft of the earplug. This rear member is made of a relatively hard polymeric material to aid in inserting the earplug into the ear canal. The other front member forming the earplug is made of a relatively soft resilient material so as to be comfortable within the interior of the ear. The forward end of the earplug has a bulbous outer configuration and with at least one flange located rearward of the bulbous end so as to have a tighter sealing relationship with the walls of the earplug.

This two-piece construction increases the cost of the earplug since the separate pieces must be separately injection molded and must then be assembled to form the earplug. The combination of the two materials requires additional labor and handling in manufacturing and thereby increases the cost relative to a one-piece earplug injection molded out of a single material. It would be desirable to achieve the benefits of the earplug of U.S. Pat. No. 5,957,136 without the added cost of molding and assembly.

SUMMARY OF THE INVENTION

The present invention provides for a one piece injected molded thermoplastic elastomer earplug which is comfortable in use and yet has a rear portion formed as an outwardly extending cup shaped flange suitable to receive the finger of the user of the earplug to form a rigid rear portion so that the earplug can be inserted deeply and easily into the ear. This structure provides for a proper acoustic sealing relationship with the walls of the ear canal and thereby provide for high attenuation of exterior noise to the interior of the ear.

DETAILED DESCRIPTION OF THE PREFERRED EMBODIMENT

As can be seen in FIGS. 1 through 4, an earplug 10 of the present invention is formed by injection molding in a single operation to have two portions 12 and 14 and with portion 12 forming a forward portion and portion 14 forming a rearward portion. The forward portion 12 is to be inserted into the ear canal and with the rearward portion 14 formed as a cup shaped flange to receive a finger of the user to facilitate the insertion of the earplug into the ear canal.

Figure 1:
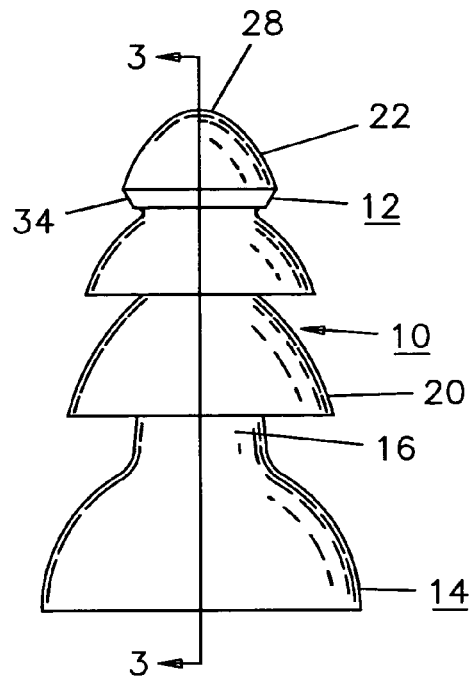
FIG. 1 is an elevational view of the earplug of the present invention.
Figure 3:
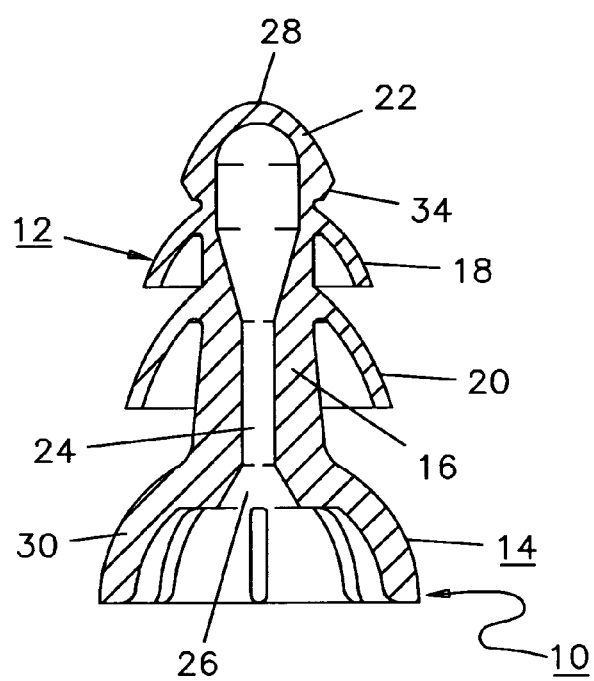
FIG. 3 is a cross-sectional view of the earplug of the present invention taken along lines 3—3 of FIG. 1.
Figure 2:
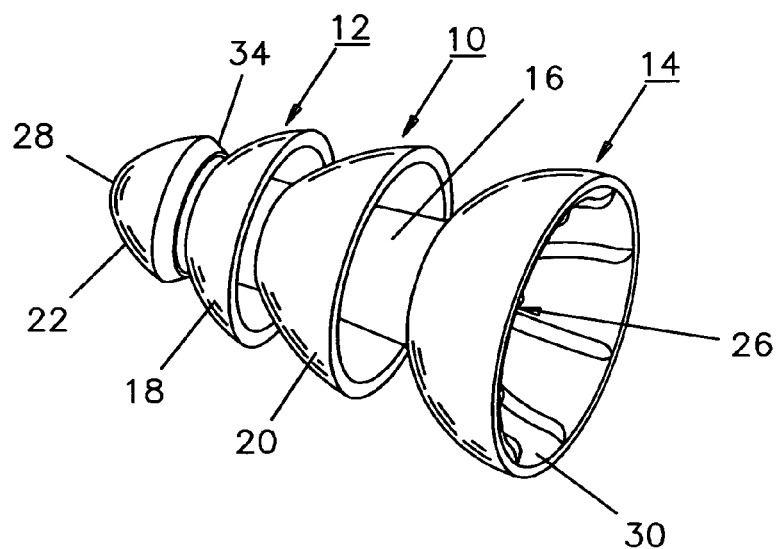
FIG. 2 is a rear perspective view of the earplug of the present invention and with a cup shaped flange extending at the rear portion of the earplug.

The portion 12 of the earplug 10 is formed of a shaft section 16, a pair of flanges 18 and 20 and a forward curved front end 22 preferably formed as a bulbous end portion. The flanges 18 and 20 as well as the curved front end 22 each have a generally rounded cone configuration and extend rearward to be received within the ear canal and provide sealing to the walls of the ear canal. As can be seen in FIG. 3, the member 12 has a hollow interior channel 24 which extends the length of the member 12 and has an open end 26 and a closed end 28, conforming to the front end 22.

Figure 4:
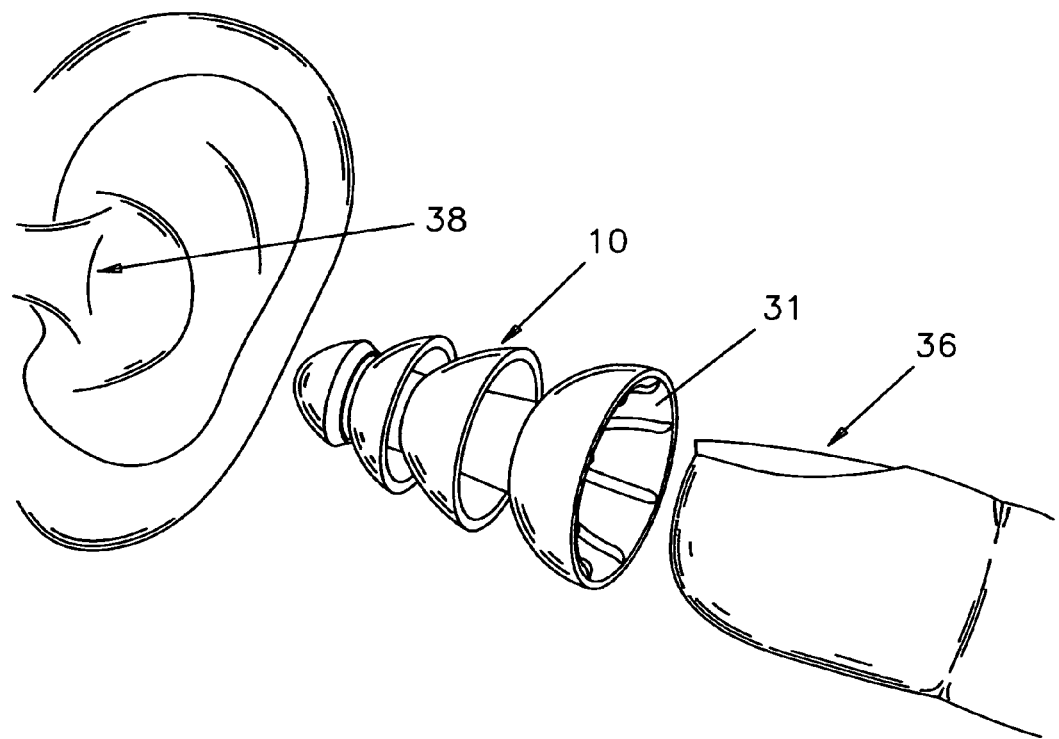
FIG. 4 is a perspective view of a user of the earplug with an index finger positioned to be inserted in the cup shaped flange of the earplug for insertion of the earplug into the ear canal of the user.

The portion 14 is formed as a cup shaped flange 30 and extends from the rear end of the shaft 16. As shown in FIGS. 3 and 4, the cup shaped flange is suitable for receiving the finger of the user, preferably the index finger so that the user can use the finger in place of the stem shown in the prior art. Because of the curvature in the shape of the cup, the user's fingertip can reach a proximity that is closer to the insert end of the earplug than an earplug with a traditional stem design. By decreasing the distance between the fingertip and the end of the earplug, the user gains leverage and control for insertion. This allows the user to easily insert an earplug made of very soft comfortable polymer.

In addition, the cup shaped flange 30, which radiates in a circumference around the center longitudinal axis of the earplug and extends outward, can be used both as an additional sealing flange for improved sound attenuation and as a handle to remove the earplug. The size of the cup shape flange can have an outside diameter in a range of ¼ to ¾ inch. A more optimal range to accommodate the fingertip of the average user would be ⅜ to ⅝ inch and with a preferred size being ½ inch plus or minus 1/16 inch. It is to be appreciated that although the cup shaped flange is shown to be round, the cup shaped flange may have other configurations as long as it can accommodate the fingertip of the user. For example, the cup shaped flange may be square, triangular, rectangular or any other regular or irregular configuration.

The hollow interior channel 24 also allows the flanges 18 and 20 to also have the ability to collapse even further so as to make the earplug very comfortable when the bulbous end 22 and the flanges 18 and 20 lie against the walls of the ear canal. It should also be noted that the curved front end 22 includes a chamfer, designated by reference numbers 34, and the flanges 18 and 20 may also include chamfers, which chamfers reduce sharp edges that would tend to be irritating in the ear canal.

The earplug of the present invention can be fabricated by any suitable polymer molding techniques and preferably by injection molding. It is important that the earplug be constructed of the proper resilient polymer material such as thermoplastic elastomer (TPE) generally described as a synthetic rubber like material that can be molded so as to have the softness at the end of the earplug that is inserted into the ear. For example the member 12 and specifically the front end 22 and flanges 18 and 20 should be formulated of material that has a Shore A Durometer hardness value (by the technique of ASTM 2240-81) of between about 10 and 30 and preferably between 15 and 25. In a preferred embodiment the member 12 can have a Shore A Durometer hardness value of approximately 21 to 22.

In the present invention when a fingertip 36 of the user is positioned to be is inserted into the cup shaped flange 30, as shown in FIG. 4, this provides for the rear end of the earplug being stiff to aid in insertion of the earplug into an ear canal 38 while the front portion of the earplug 10 is more compliant and comfortable in the ear canal. In addition, the cup shaped flange 30, which radiates in a circumference around the center longitudinal axis of the earplug and extends outward, can be used both as an additional sealing flange for improved sound attenuation and as a handle to remove the earplug.

There are many known resilient polymeric materials that may be used to form the earplugs of the present invention. For example, natural rubber, neoprene rubber, SBR rubber (styrene block copolymer compounds), silicone rubber, EPDM rubber, polybutadiene rubber, polyvinylchloride elastomers, polyurethane elastomers, ethylene vinyls, acetate elastomers, elastomers based on acrylic acid precursors and vinylhalide polymers may all be generally suitable materials which can be used to provide the necessary Shore A Durometer values. As preferred materials the present invention contemplates using a SBR rubber for the earplug 10.

The present invention therefore provides for an earplug with one rear cup shaped flange portion, in combination with the fingertip of the user, forming a firm handle for the insertion of the front portion of the earplug that is inserted into the ear channel. In addition, the cup shaped flange radiates in a circumference around the center longitudinal axis of the earplug and extends outward, and is used both as an additional sealing flange for improved sound attenuation and as a handle to remove the earplug.

The earplug has a curved front end and flanges to provide for a sealing of the earplug within the ear canal and with a comfortable fitting of the earplug in the ear canal. The present invention therefore provides for a unique structure easily injection molded in a cost efficient manner of a soft polymer that provides for an earplug having all the desired characteristics that are lacking in the prior art.

Although the present invention has been described with reference to a particular embodiment, it should be appreciated that various adaptations and modifications may be made. For example, the earplug is shown to include the hollow interior channel 24 but this channel could be eliminated and the earplug be molded as a solid member. The earplug would thereby be less compliant at the front portion but the Shore A Durometer hardness value may be adjusted to compensate for this increase in stiffness. The invention is only to be limited by the appended claims.

I claim:

1. An earplug composed of an injected molded resilient polymeric material for insertion into an ear canal by a fingertip of a user, including an elongated member having a nose portion formed as a curved front end, an open cup shaped rearward extending flange located at the end of the elongated member opposite to the nose portion and with the open cup shaped rearward extending flange configured to receive the fingertip of the user, the elongated member also including at least one hollow rearward extending flange element located intermediate the nose portion and the open cup shape flange, both the nose portion and the at least one flange element having a generally curved shape to extend into and conform to the wall of the ear canal, and with the diameter of the curved shape of the front end increasing progressively from the nose end to a maximum diameter and with the diameter of the at least one hollow rearward extending flange element also increasing progressively to a maximum diameter larger than the maximum diameter of the nose end, and the earplug composed of a resilient polymer material having a relatively low Shore A Durometer hardness value and the cup shape flange portion with the inserted fingertip of the user forming a handle of greater stiffness to enable the earplug with the relatively low Shore A Durometer hardness value to be more easily inserted into the ear canal.

2. The earplug of claim 1 wherein the elongated member includes at least two hollow rearward extending flange elements of serially increasing diameters and with the nose portion having a smaller diameter than any of the flange elements.

3. The earplug of claim 1 wherein the open cup shaped rearward extending flange radiates outwardly in a circumference around the center longitudinal axis of the elongated member to form an additional sealing flange for sound attenuation.

4. The earplug of claim 1 wherein the earplug is composed of a resilient polymeric material having a Shore A Durometer hardness value of between 10 and 30.

5. The earplug of claim 1 wherein the earplug has a Shore A Durometer hardness value of between 15 and 25.

6. The earplug of claim 1 wherein the earplug has a Shore A hardness value of 21 to 22.

7. The earplug of claim 1 wherein the earplug is composed of a rubber.

8. The earplug of claim 1 wherein the earplug 1 is composed of a SBR rubber.

9. The earplug of claim 1 wherein the open cup shaped rearward extending flange radiates outwardly in a circumference around the center longitudinal axis of the elongated member and has a diameter between ¼ to ¾ inch.

10. The earplug of claim 1 wherein the open cup shaped rearward extending flange radiates outwardly in a circumference around the center longitudinal axis of the elongated member and has a diameter between ⅜ to ⅝ inch.

11. The earplug of claim 1 wherein the open cup shaped rearward extending flange radiates outwardly in a circumference around the center longitudinal axis of the elongated member and has a diameter of ½ inch, plus or minus ¹⁄₁₆ inch.

12. An earplug composed of an injected molded resilient polymeric material for insertion into an ear canal by a fingertip of a user, including
a first hollow member having a closed curved front end and an open end and with the closed end having a thin walled cone shaped configuration substantially uniform in thickness at the closed end,
at least one flange member extending from the first hollow member and having a similar cone shaped configuration as the bulbous closed end of the hollow member but larger in maximum diameter and located rearward of the closed end, and with the diameter of the closed curved front end increasing progressively to a particular diameter less than the maximum diameter of the flange member and then decreasing to meet the flange member,
an open cup shaped rearward extending flange located at the end of the elongated hollow member opposite to the nose portion and with the open cup shaped rearward extending flange configured to receive the fingertip of the user, and
the earplug composed of a resilient polymer material having a relatively low Shore A Durometer hardness value and the cup shape flange portion with the inserted fingertip of the user forming a handle of greater stiffness to enable the earplug with the relatively low Shore A Durometer hardness value to be more easily inserted into the ear canal.

13. The earplug of claim 12 wherein the elongated hollow member includes at least two rearward extending flange members of serially increasing diameters and with the closed end of the hollow member having a smaller diameter then than any of the flange members.

14. The earplug of claim 12 wherein the open cup shaped rearward extending flange radiates outwardly in a circumference around the center longitudinal axis of the elongated hollow member to form an additional sealing flange for sound attenuation.

15. The earplug of claim 12 wherein the earplug is composed of a resilient polymeric material having a Shore A Durometer hardness value of between 10 and 30.

16. The earplug of claim 12 wherein the earplug has a Shore A Durometer hardness value of between 15 and 25.

17. The earplug of claim 12 wherein the earplug has a Shore A hardness value of 21 to 22.

18. The earplug of claim 12 wherein the earplug is composed of a rubber.

19. The earplug of claim 12 wherein the earplug 1 is composed of a SBR rubber.

20. The earplug of claim 12 wherein the open cup shaped rearward extending flange radiates outwardly in a circumference around the center longitudinal axis of the elongated hollow member and has a diameter between ¼ to ¾ inch.

21. The earplug of claim 1 wherein the open cup shaped rearward extending flange radiates outwardly in a circumference around the center longitudinal axis of the elongated hollow member and has a diameter between ⅜ to ⅝ inch.

22. The earplug of claim 1 wherein the open cup shaped rearward extending flange radiates outwardly in a circumference around the center longitudinal axis of the elongated hollow member and has a diameter of ½ inch, plus or minus ¹⁄₁₆ inch.

23. An earplug composed of an injected molded resilient polymeric material for insertion into an ear canal by a fingertip of a user, including
a first hollow member having a bulbous closed end and an open end and with the closed end having a thin walled cone shaped configuration substantially uniform in thickness at the closed end,
at least one flange member extending from the first hollow member and having a similar cone shaped configuration as the bulbous closed end of the hollow member but larger in maximum diameter and located rearward of the closed end, and with the diameter of the bulbous closed end increasing progressively to a particular diameter less than the maximum diameter of the flange member and then decreasing to meet the flange member, and wherein the bulbous end has a rear chamfered end so as to reduce sharp edges when the earplug is inserted into the ear canal,
an open cup shaped rearward extending flange located at the end of the elongated hollow member opposite to the nose portion and with the open cup shaped rearward extending flange configured to receive the fingertip of the user, and
the earplug composed of a resilient polymer material having a relatively low Shore A Durometer hardness value and the cup shape flange portion with the inserted fingertip of the user forming a handle of greater stiffness to enable the earplug with the relatively low Shore A Durometer hardness value to be more easily inserted into the ear canal.

24. An earplug composed of an injected molded resilient polymeric material for insertion into an ear canal by a fingertip of a user, including
a first hollow member having a bulbous closed end and an open end and with the closed end having a thin walled cone shaped configuration substantially uniform in thickness at the closed end, at least one flange member extending from the first hollow member and having a similar cone shaped configuration as the bulbous closed end of the hollow member but larger in maximum diameter and located rearward of the closed end, and with the diameter of the bulbous dosed end increasing progressively to a particular diameter less than the maximum diameter of the flange member and then decreasing to meet the flange member, an open cup shaped rearward extending flange located at the end of the elongated hollow member opposite to the nose portion and with the open cup shaped rearward extending flange configured to receive the fingertip of the user, and wherein the open cup shaped rearward extending flange radiates outwardly in a circumference around the center longitudinal axis of the elongated hollow member to form an additional sealing flange for sound attenuation and for removal of the earplug after use.

\* \* \* \* \*